(12) United States Patent
Kemmish, Jr.

(10) Patent No.: US 10,908,144 B2
(45) Date of Patent: Feb. 2, 2021

(54) STACKS OF COALIGNED NANOPORES AND FABRICATION AND USES THEREOF

(71) Applicant: Stanley Kent Kemmish, Jr., Hayward, CA (US)

(72) Inventor: Stanley Kent Kemmish, Jr., Hayward, CA (US)

( * ) Notice: Subject to any disclaimer, the term of this patent is extended or adjusted under 35 U.S.C. 154(b) by 17 days.

(21) Appl. No.: 15/975,764

(22) Filed: May 9, 2018

(65) Prior Publication Data

US 2018/0328909 A1 Nov. 15, 2018

Related U.S. Application Data

(60) Provisional application No. 62/503,340, filed on May 9, 2018.

(51) Int. Cl.
| | |
|---|---|
| *G01N 33/487* | (2006.01) |
| *C12Q 1/6869* | (2018.01) |
| *B01D 67/00* | (2006.01) |
| *B82Y 15/00* | (2011.01) |
| *G01N 27/49* | (2006.01) |
| *B82Y 35/00* | (2011.01) |
| *B82Y 40/00* | (2011.01) |
| *G01N 21/64* | (2006.01) |
| *C12Q 1/6825* | (2018.01) |

(52) U.S. Cl.
CPC ... *G01N 33/48721* (2013.01); *B01D 67/0062* (2013.01); *C12Q 1/6869* (2013.01); *B82Y 15/00* (2013.01); *B82Y 35/00* (2013.01); *B82Y 40/00* (2013.01); *C12Q 1/6825* (2013.01); *G01N 21/6428* (2013.01); *G01N 27/49* (2013.01)

(58) Field of Classification Search
None
See application file for complete search history.

(56) References Cited

U.S. PATENT DOCUMENTS

| | | | |
|---|---|---|---|
| 2003/0080042 A1* | 5/2003 | Barth | B01D 67/0058 210/321.84 |
| 2003/0190632 A1* | 10/2003 | Sosnowski | B01J 19/0046 435/6.11 |
| 2005/0014162 A1* | 1/2005 | Barth | B01L 3/502761 435/6.11 |
| 2012/0170034 A1* | 7/2012 | Van Dorpe | G01N 21/554 356/301 |

(Continued)

*Primary Examiner* — Edwin C Gunberg

(57) ABSTRACT

Disclosed is an improved form of nanopore-based molecular sensor: a stack of coaligned nanopores in an equivalent number of directly stacked membranes. One or more of the membranes is moved laterally, altering the volumetric shape and thus the sensing characteristics of the passage. This allows at least three major improvements over existing nanopore sensors: 1) volumetrically tunable sensors allow sensing over a wider range of analyte sizes, 2) volumetric shape changes allow a a novel form of translocation control over transiting molecules, enabling more information to be derived from single molecules through interactions with the walls of the passage and controllable alterations in the local electrostatic and hydrodynamic environment, and 3) volumetric shape changes allow regeneration of an appropriate sensor geometry in the event of corrosion or clogging, greatly extending the useful lifetime of individual sensors.

16 Claims, 4 Drawing Sheets

(56) References Cited

U.S. PATENT DOCUMENTS

2015/0028846 A1\* 1/2015 Zhu .................... G01N 27/3275
324/71.5
2015/0377830 A1\* 12/2015 Baldauf ............... C12Q 1/6827
204/451

\* cited by examiner

STACKS OF COALIGNED NANOPORES AND FABRICATION AND USES THEREOF

BACKGROUND OF THE INVENTION

Nanopore-based molecular sensing is an emerging technology of great importance to biomedical research, synthetic biology, and molecular engineering. Commercial nanopore sensors using nanopores of fixed sizes ("static nanopores") have become available, but these have significant limitations addressed by the disclosed invention. Static nanopores are limited in their range of detection to molecules that are similarly sized, and the present disclosure describes methods for fabricating and using stacked nanopores that allow dynamic retuning of their volumetric shape in order to closely accommodate and measure a wide range of biomolecules. Further, static nanopores suffer from both corrosion and clogging, both of which can be greatly mitigated by the described methods.

We urgently need greater power to explore and manipulate biological, chemical, and physical systems both for basic research and for commercially and socially valuable diagnostics, sensing, and manufacturing applications. The invention involves novel methods for sensing, sorting, and manipulating atoms and molecules. Billions of dollars and decades of effort have been spent on developing sensing/sorting capabilities based on passing analytes through nanometer scale holes, i.e., nanopores and nanochannels. The present disclosure teaches methods to create variable stacked nanopore passages (and more broadly, channels at scales from the micron scale down to sub-angstrom scales) that can be opened and closed with extreme precision to form apertures of different sizes and shapes.

BRIEF SUMMARY OF THE INVENTION

The invention comprises sensing tools and methods in which the three dimensional characteristics of a nanoscale passage for sensing molecules can be dynamically retuned in order to derive more information from individual molecules as well as to derive information from a wider range of sizes of molecules, while also allowing for regeneration of an appropriate sensing geometry in response to corrosion and/or clogging of the passage. In a preferred embodiment, three membranes are stacked on top of each other in a manner permitting their free lateral movement, a nanometer or micron-scale hole is formed through the three membranes, and then at least one of the membranes is moved laterally to change the effective volumetric shape of the passage.

DISCLOSURE OF INVENTION

Figure 1:
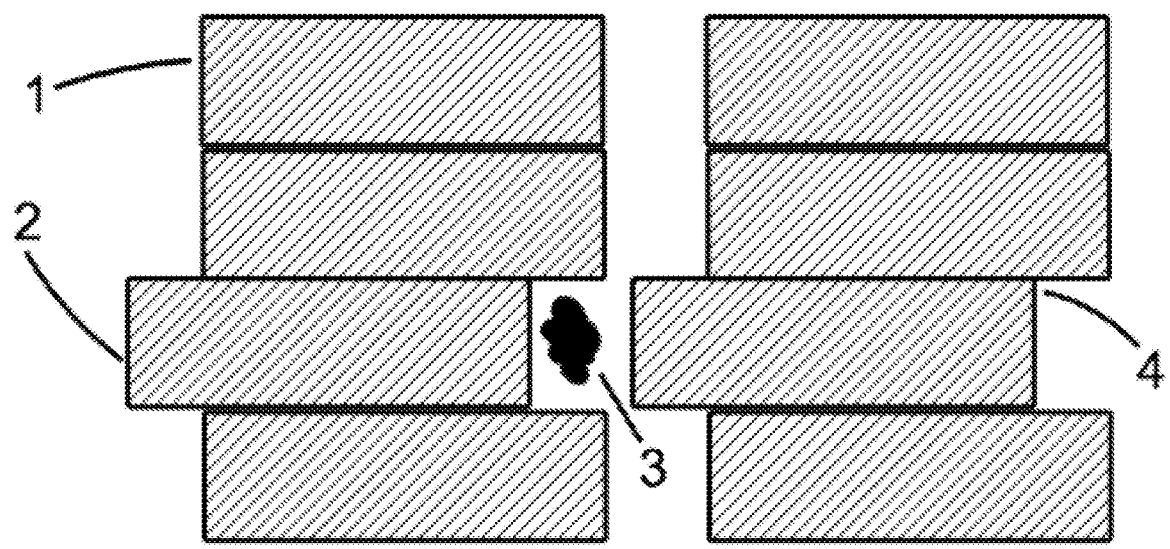
FIG. 1 illustrates a stack of four nanopores with equivalent dimensions.

A barrier, comprising multiple stacked membranes, is created between two volumes, such that in the absence of an unobstructed passage in the barrier material little or no transit of particles occurs. Each membrane contains openings that will permit transit of particles when not occluded by an impermeable portion of another layer or of other layers. Particle transit occurs when openings in a separate layer or layers are juxtaposed by relative motion. A major novel insight of the invention is the idea of moving and juxtaposing three or more layers relative to each other in order to dynamically specify the volumetric shape formed by their relative juxtaposition, and in particular the use of three or more layers rather than only two in order to usefully affect both the longitudinal and lateral volumetric dimensions of the stacked passage.

Stacked nanopores for sequencing allow slowing down, capture, and oversampling of individual bases by altering the size of the pore while the ssDNA molecule is transiting the pore, addressing multiple longstanding challenges in the nanopore sequencing approach. A major general advantage of the invention is its applicability to a wide range of analytes from single atoms up to entire cells with a single sensing device. Several aspects of the invention can be implemented with a wide variety of materials, material dimensions, number of holes in each layer, detection schemes, and types of matter within the chambers.

Membrane materials include any materials than be isolated in planar form, perforated in some manner, and moved relative to other barrier layers without excessive friction. Examples include but are not limited to graphene, silicon nitride, silicon carbide, and Teflon.

Material dimensions may be arbitrarily thin or thick while still offering advantages inherent to the approach. For DNA sequencing and accurate sizing/structure determination of molecules, graphene may be ideal for both transverse current and ionic blockade approaches. However, thicker materials may be utilized as well.

The dimensions of the holes in individual membranes may be as small as their chemical composition allows (single missing carbon atoms in the case of graphene's hexagonal lattice of sp2-hybridized carbons) and as large as would be consistent with being able to be manipulated and placed as a barrier material with appropriate mechanical properties.

One or more layers can be coplanar but physically separate, and their edges may be brought closer together than the width of a single atom to form part of the occlusion present in a single passage.

Nanopore stacks can perform useful sensing, separation, and filtration activities between chambers containing gas or liquids. In one embodiment, gas molecules can be separated based on kinetic energy by forming a passage with extreme precision, such that only molecules with sufficient energy can transit the pore, while molecules of the same elemental and chemical makeup do not transit the pore, by requiring that a molecule impart enough energy to the edges of a pore to slightly displace the atoms at the edges to permit passage. Alternately, tunneling current detection can be used to determine the transit time of an individual particle through the pore, triggering the opening of the passage further along the path of transit, so that only particles of a certain speed are collected in a third chamber.

It is advantageously consistent with the methods of the invention to allow one or more membranes to contain more than one hole or channel, allowing holes and channels to be formed in individual layer materials using less precise, "shotgun" style methods (e.g., controlled dielectric breakdown). This relaxes constraints on precisely localized hole placement, because useful tunable stacked passage may be formed by simply moving one or more layers relative to the others until a current is detected (in the case of ionic current flow detection schemes in aqueous implementations.)

Membranes may be independently moved and actuated to create a precise 3 dimensional chamber in which a molecule may be "tumbled" and manipulated in order to more precisely determine its structure, shape, charge characteristic, and size, allowing for gated passage of the molecule in the case in which the stacked passage is put to use as a selective filtering device.

A further particular advantage of the invention over non-size-tunable nanopores is in the capture efficiency of the approach for DNA and other molecules. A major drawback to small, static nanopores for DNA sequencing and other forms of molecular sensing is the time required for molecules to diffuse near the pore and be drawn through under electrophoretic force. In the case of the invention, a passage can at in one part of its geometry be significantly larger than the ideal diameter for sensing of a target analyte, and upon sensing a weak signal corresponding to the entrance of the target analyte to the pore entrance, the dimension can be rapidly reduced so as to provide an ideal diameter for sensing the target. This largely solves the problem of "idle pores" in multipore arrays, i.e. pores not being actively used for sensing at a given moment, increasing the overall throughput of a multipore or single pore device.

Still another significant advantage of the invention is its ability to compensate for corrosion phenomena. In particular, static solid state pores are known to degrade in solution at a rate having a negative impact on overall device efficiency and lifetime. The invention compensates for this phenomenon, as simply moving and calibrating the stack can mitigate the effects of corrosion at the edges of the individual nanopores within the stack. The volumetric shape of the stacked passage can be restored to useful, targeted diameter shapes and sizes after corrosion is detected.

One such non-limiting detection modality is the optical detection of ionic current flux using fluorescent dyes that are sensitive to ions. In this modality, individual stacks do not need to be electrically isolated. Optical detection by this modality has been achieved in the labs of Meni Wanunu and Hagan Bayley, among others.

A simple device may be constructed using the methods of the invention by taking three silicon nitride layers containing micropores spaced 2-20 um apart and moving them in apposition to each other so as to create an opening ideal for sequencing either unlabeled or labeled ssDNA or osymylated DNA or DNA with large labels attached (e.g., undeca-gold, though other examples will occur to PHOSITA) and applying a voltage so as to determine the base sequence following the optical detection techniques pioneered by the labs of Wanunu, Bayley, and others.

Of note in such a detection modality is the possibility of using optical detection on both cis and trans chambers of a stacked nanopore sensing apparatus, with the use of dye molecules sensitive to either cations or anions on either side. Another embodiment of the invention comprises the differential detection of ions of significantly different radius in order to activate the fluorescence of differently sensitive dye molecules, an approach with the potential to enhance the signal-to-noise ratio of the readout. Further, osmylating DNA as pioneered by Kanavarioti et al. may be advantageously used in this setting.

An even further advantage of the invention over static pores is identified in the phenomenon of pore-clogging, which has a major effect on the usability and lifetime of other nanopore approaches. Both solid-state and biological nanopores suffering from clogging in solution, which can sometimes be mitigated by reversing the current, but which also often render an individual pore indefinitely nonfunctional. In addition to current reversal strategies to mitigate clogging phenomena, stacked nanopores may also simply open, shut, or vibrate in order to release the clog. In cases where this does not avail, the stack may continue to function by simply compensating for the presence of clogging material by increasing its volume and using the empty space relative to the clogging material as a pore of suitable, tunable diameter.

Of note is that such "releasable clogging" can also be taken advantage of in order to acquire more data about the clogging material itself, which may comprise target analytes.

Of extraordinary interest from both a theoretical and practical perspective is the invention's ability to move materials relative to each other with fine control in the case where the particular apposition of membranes at a particular moment in time yields a characteristic signal detectable by Raman spectroscopy. In the case of graphene layers, Raman spectroscopy is well-known to be able to distinguish the "stacking order" of multiple layers in terms of the geometry of hexagonal carbon units in one layer relative to apposing layers. This increases the capability of the invention to fine-tune feedback loops between applied motion and useful knowledge of how much the layers have actually shifted under that applied motion. This also introduces the capability to detect local mechanical or electronic perturbation at the pore itself caused by passage of analytes that interact with the edges of stacked passage.

Alternative embodiments may contain individual layers of either the same or different materials, with any number of holes or channels. Individual layers within the barrier stack may consistent of conductive gapped nanowires, allowing the passage to take advantage of sensing via tunneling current and other physical phenomena.

A remarkable advantage of the invention relies on the fact that physical movement of layer materials may be actuated with sub-angstrom precision using a variety of methods (e.g., piezopositioning) known to those having ordinary skill in the art of electromechanical motion actuation. Thus a single stacked nanopore passage may trap, gate, sense, and otherwise manipulate individual particles with a structural precision corresponding potentially to picometer distances.

Another general advantage of the invention is the potential to perform mechanochemical manipulations on particles occupying the pore. In one embodiment, scission of DNA molecules could be effected through mechanical force, with the shutting off of the passage analogous to the action of a guillotine. In one embodiment of the invention, three layers of single-layer graphene are placed against each other, with each layer containing a hole or holes that initially are not juxtaposed so as to allow passage of particles between the separate volumes. As the holes are juxtaposed to form an aperture, particles are then able to pass through all three layers of graphene. This is one of many embodiments that allows for sequencing of DNA molecules, using any of several base detection schemes that have been proposed (ionic current occlusion, transverse current detection, etc.), but with the advantage of a pore whose geometry can be precisely and dynamically controlled in feedback loops with the sensing of particles in the pore.

One embodiment of the invention as described in the previous paragraph is described more fully in the present paragraph. Nanometer-scale holes are formed in graphene layers (either monolayers or multiple layers) using a variety of methods known to PHOSITA (e.g., colloidal lithography, ion beam milling, TEM drilling, photothermal melting of gold nanorods, etc.) In some embodiments multiple holes may be present. Three or more layers of material are then placed in contact and at least one layer is tethered physically to an actuator that can be electronically controlled to push and pull the tethered layer relative to other layers. Graphene presents an advantageous material for nanopore-based sensing due to its low permeability, its atomically thin dimensions relative to an ionic current flow, and its electronic properties in the case of transverse current detection. Further, an advantage for a stacked-nanopore-based approach in particular is graphene's strong mechanical properties and its low friction coefficient relative to other graphene surfaces. The stack of membranes forms an impermeable barrier between two compartments, designated as cis or trans, with atoms or molecules to be analyzed or separated introduced into the cis compartment, and electrodes in both compartments so that variable current of an ions can be measured. In this approach, ssDNA molecules to be sequenced are introduced to the cis compartment, which also contains charged ions, and a sensitive current detection scheme is employed to measured the changes in ionic current that result from occlusion of the passage. As in classical nanopore based sequencing with current occlusion detection, a current change is caused in a manner characteristic of each type of base that transits the opening.

The methods of the invention offer significant advantages to nanopore-based sequencing methods. Cheap and scalable methods to fabricate monodisperse consistently sized holes in appropriate materials have not been reported. The invention allow inconsistency in the diameter size distribution of the pores or channels in individual layers, because precise aperture formation can be achieved after using chemical/electrical/mechanical methods to make the holes or channels in each layer by calibrating the degree and direction of juxtaposition in the individual layers. The size and shape of individual holes can be determined through calibration of passage volume using (as a non-limiting example) ionic current measurements as a proxy. This relaxes the constraints on scalable pore and channel fabrication in appropriate materials.

FIG. 1 shows a cross section of a stack of nanopores in slidable, stacked membranes in which the nanopores have similar lateral and longitudinal dimensions. This represents a general abstract scheme for the construction and use of stacked sliding-occlusion-based nanopore passages. The figure is not to scale (either in absolute terms or in terms of the components relative to each other) and does not represent any limitations on the geometry or material compositions of the invention. It is worth noting that none of the figures present in this disclosure are intended to show scale accurately in either absolute or relative terms.

1 represents one of the four membranes, which in this representation are presumed to have similar thicknesses. The membranes chosen may consist of any materials that are generally impermeable to the transit of particles between chambers when present in a continuously solid form. 2 represents one of the four membranes being displaced, causing the edges of its associated nanopore to partially occlude the entrances to the nanopores adjacent to it in the stack. 3 represents a molecule transiting the passage. If the drawing were intended to show realistic relative scaling for the size of the molecule, its position as shown within the nanopore, and the relative dimensions of the nanopore as shown, the molecule shown could non-limitingly represent a large virus approximately 300 nanometers at its widest point, with the nanopores shown representing openings on the order of 500 nanometers, and the membranes shown representing, as a non-limiting example, 500 nanometer thick silicon nitride. 4 represents the interface between two of the membranes, which should allow consistent positioning and repositioning of the membranes relative to each other, and which may comprise surface modifications with anti-stiction coatings such as octadecyltrichlorosilane and many others known to PHOSITA (Person Having Ordinary Skill in The Art.)

Not shown are obvious means by which motion of individual layers can be coupled to a means of actuation. In a simple embodiment, this may be one or more rigid arms physically tethered or in mechanical contract with one or more of the membranes in the stack.

Not shown, and described herein only to more fully explain the context of the invention, are means for measuring changes that occur as a result of the transit of a molecule through the passage and its interaction with the passage walls. These may include picoammeters or patch clamp amplifiers in the case of current modulation detection schemes, and controls for focusing and taking images in the case of microscopy.

Figure 2:
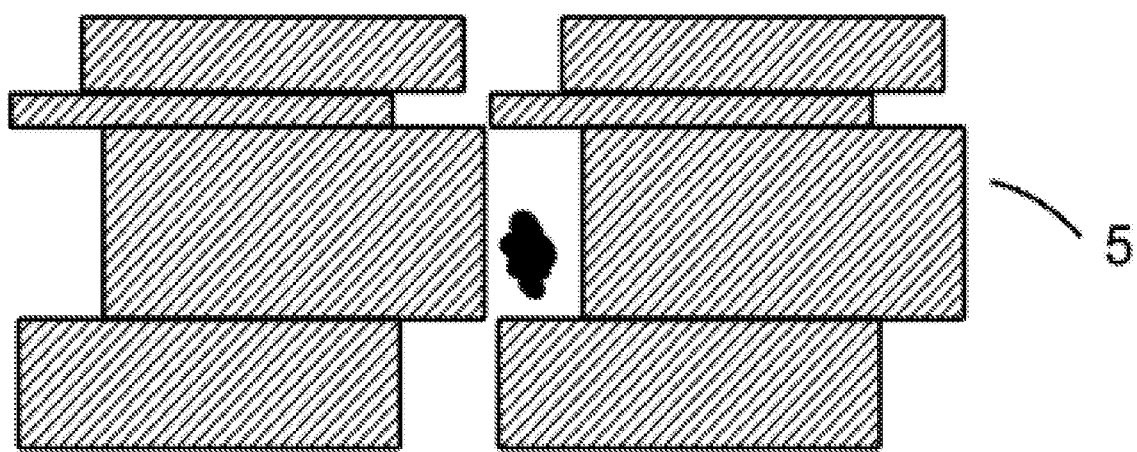
FIG. 2 illustrates a stack of four nanopores with different longitudinal dimensions.

FIG. 2 shows a cross section of a stack of nanopores in slidable, stacked membranes in which the nanopores have similar lateral dimensions but different longitudinal dimensions. 5 represents a membrane significantly thicker than the other membranes in the stack, which offers the advantage of a longer time resident in one portion of the passage upon reversal of current or the so-called "ping-pang" oversampling approach, which allows extremely precise measurements to be made of hydrodynamic radius and other characteristics that allow a molecule to be identified and measured.

Figure 3:
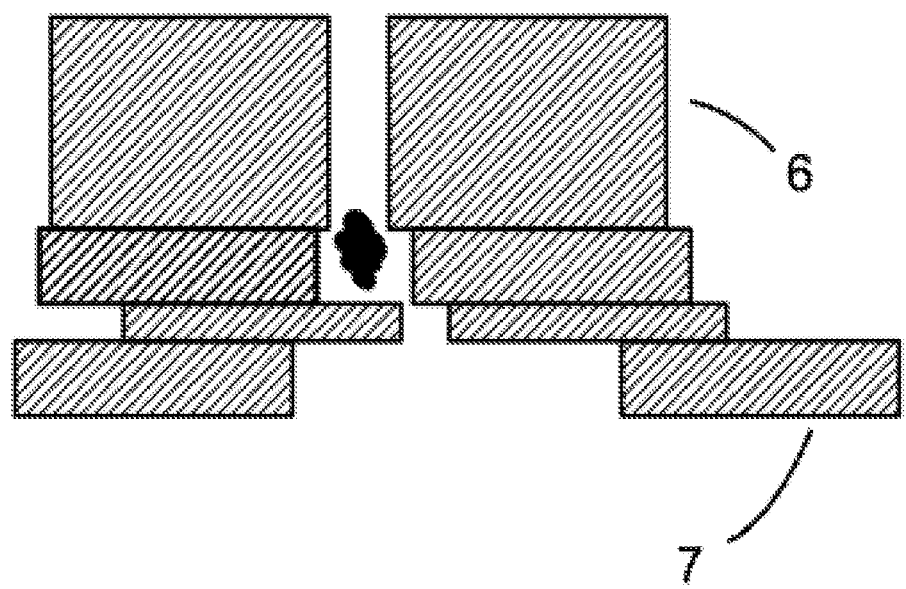
FIG. 3 illustrates a stack of four nanopores with different longitudinal dimensions and diameters.

FIG. 3 shows an embodiment of the invention in which both the lateral and longitudinal dimensions of the stacked nanopores and associated membranes differ. 6 is a membrane containing a high-aspect ratio nanopore, whereas 7, on the opposite side of the same stack, contains a wide, low-aspect ratio nanopore. Compared to FIGS. 1 and 2, the configuration of 3 offers more opportunities for reconfigurable regeneration of clogged or corroded pore elements.

Figure 4:
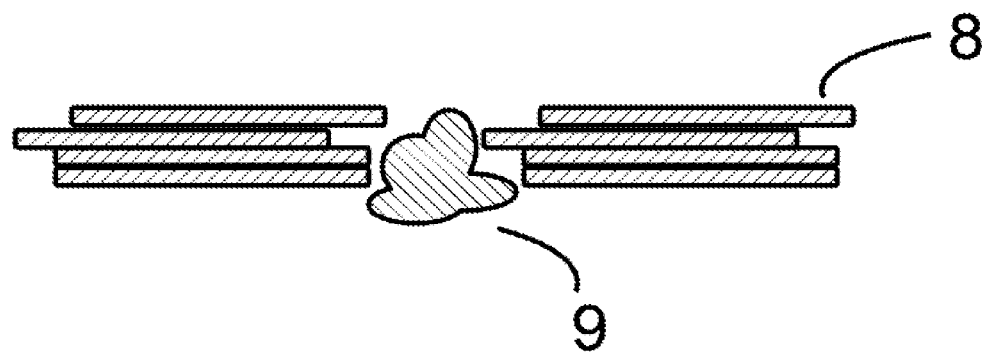
FIG. 4 illustrates a stack of four nanopores in ultra-thin membranes.

FIG. 4 illustrates a stack of extremely thin membranes (8 is the top one in the shown orientation) in which the stack of nanopores are close enough longitudinally that they are able to probe a single molecule 9, allowing rich structural information, like that offered by STM or AFM, to be obtained.

BEST MODES FOR THE INVENTION

We herein disclose a most preferred embodiment of the invention in sufficient detail for PHOSITA to perform molecular sensing with a stack of coaligned nanopores.

Minimal experimental apparatus required includes two 3-axis nanopositioners with at least 10 microns of travel (Mad City Labs), a patch clamp amplifier for setting voltage and measuring current changes (Elements, Inc.), and a fluid cell to which stacks of membranes can be attached and into which electrodes can be inserted. The experimenter should also have access to 1 M potassium chloride and an appropriate mechanical setup common to nanopore work (Faraday cage, vibration isolation, etc.)

The experimenter may obtain convenient sources of many-layer graphene from (e.g.) ACS chemicals. The many-layer graphene should be cut into three different square portions and placed into three separate small, mechanically rigid frames of three different sizes, such that they can be set into each other in such a way that at least two nanopositioning actuators may push against each frame and thereby affect relative motion of its attached graphene film without interfering with the motion or actuation of the other frames and membranes. Actuators transmitting motion from the nanopositioning cubes and the frames can be made of rigid, sharp metallic materials, in particular, we have found that 0.131" framing nails serve this purpose nicely. Either marine epoxy or silicon may be used as adhesives between the frames and the nails. The nails may be attached to custom 3D printed or machined polycarbonate holders that can be screwed into the commercial nanopositioners. The "bottom" frame with graphene does not need to be moved to implement the invention in this mode, so the two "top" frames should be the ones attached to the actuator nails.

In this embodiment, fluid cell construction must be carefully considered so as to prevent unwanted leakage. The bottom frame with its associated graphene multi-layer should be directly apposed to an opening in the bottom fluid cell, and the top frame and its associated fluid cell should be apposed to a top fluid cell into which an Ag/AgCl electrode can be inserted.

After the frames, actuators, wells, positioners, and amplifier/detector are all appropriately in place, a higher voltage is applied using a 9V battery. The electrodes connecting the patch clamp amplifier should not be in place when this is done or the process could damage the amplifier. 9V of bias should be applied in ~10 second pulses, with intermittent monitoring of current characteristics across the stack of three multi-layer-graphene membranes. The experimenter monitoring the changing current characteristics in this manner should stop applying the 9V battery electrodes when current measured by the amplifier shows an increase, corresponding to the formation of a coaligned pathway through all three multi-layer graphene membranes.

Known methods and protocols for sensing in a normal nanopore context should be employed after the step of forming the stacks of nanopores in the set of three layers of multi-layer graphene.

At this point, motion of either of the nanopositioners attached to the top two membrane frames will cause changes in the volumetric shape of the dielectically formed passages through the three membranes.

What is claimed is:

1. A stack of at least three longitudinally aligned nanopores in an equivalent number of stacked solid membranes that are free to move laterally such that moving one or more of the membranes changes the longitudinal alignment of the nanopores, thus modifying the dimensions and volumetric shape of the passage through the stacked membranes, wherein at least two of the stacked solid membranes have different thickness.

2. The stack of claim 1, wherein at least one of the plurality of solid membranes comprises an atomically thin sheets.

3. The stack of claim 1, in which at least one of the solid membranes comprises a material selected from a group of plastics consisting of polyethylene terephthalate, polyimide, polycarbonate, polycaprolactone, polyether ether ketone, polytetrafluoroethylene, and polyoxymethylene.

4. The stack of claim 1, in which at least one of the solid membranes comprises a material selected from a group consisting of silicon, silicon nitride, silicon carbide, quartz, amorphous carbon, aluminum oxide, titanium oxide, diamond, and glass.

5. The stack of claim 1, in which at least one of the solid membranes is metallic.

6. The stack of claim 1, wherein at least two of the nanopores or the plurality of stacked solid membranes have different longitudinal dimensions from each other.

7. The stack of claim 1, wherein at least two of the nanopores of the plurality of stacked solid membranes have different longitudinal dimensions and different lateral dimensions from each other.

8. A method for fabricating an adjustable passage of stacked longitudinally aligned nanopores through a plurality of stacked movable coplanar solid membranes, the method comprising: stacking a plurality of solid membranes, and forming one or more vias through the entire thickness of the stacked solid membranes.

9. The method of claim 8, wherein the vias are formed by a method selected from a group consisting of ion-beam sculpting, controlled dielectric breakdown, electron beam drilling, laser drilling, laser heating, small hole EDM, chemical etching, direct mechanical drilling, colloidal lithography, and photothermal melting of gold nanorods.

10. The method of claim 8, wherein at least one of the membranes can be displaced at least far enough that its solid portion completely covers a nanopore in an adjacent membrane within the same stack of nanopores within the stack of membranes.

11. A method for sensing molecules, comprising: mechanically adjusting a stack of at least three longitudinally aligned nanopores in an equivalent number of stacked solid membranes that are free to move laterally; wherein at least two of the stacked solid membranes have different thickness; passing molecules through the nanopores; and measuring changes that occur as a result of the molecules passing through and interacting with the stack of nanopores.

12. The method of claim 11, wherein said measuring changes comprises measuring changes in ionic current as a result of the molecules passing through and interacting with the stack.

13. The method of claim 11, wherein said measuring changes comprises measuring changes in a tunneling current passing through one or more of the membranes in the stack as a result of molecules passing through and interacting with the stack.

14. The method of claim 11, wherein said measuring changes comprises:
passing fluorescent molecules and directly imaging their passage through the stack of nanopores.

15. The method of claim 12, wherein changes in ionic current are measured electronically.

16. The method of claim 12, wherein changes in ionic current are measured optically by imaging ionically sensitive fluorescent reporter molecules.

* * * * *